US008490889B2

(12) United States Patent
Rydbom

(10) Patent No.: US 8,490,889 B2
(45) Date of Patent: Jul. 23, 2013

(54) WIND DIRECTED SCENT DISPENSER

(76) Inventor: Mark Edwin Rydbom, Meadville, PA (US)

( * ) Notice: Subject to any disclaimer, the term of this patent is extended or adjusted under 35 U.S.C. 154(b) by 52 days.

(21) Appl. No.: 13/068,269

(22) Filed: May 6, 2011

(65) Prior Publication Data

US 2011/0278371 A1 Nov. 17, 2011

Related U.S. Application Data

(60) Provisional application No. 61/395,750, filed on May 17, 2010.

(51) Int. Cl.
*A61L 9/04* (2006.01)
*A24F 25/00* (2006.01)
*B05B 1/30* (2006.01)

(52) U.S. Cl.
USPC .......... 239/37; 239/34; 239/38; 239/39; 239/48; 239/52; 239/569

(58) Field of Classification Search
USPC .............. 239/34, 37–39, 48, 52, 569
See application file for complete search history.

(56) References Cited

U.S. PATENT DOCUMENTS

| | | | | |
|---|---|---|---|---|
| 4,773,177 A * | 9/1988 | Gray et al. | | 43/1 |
| 4,937,431 A * | 6/1990 | Jameson et al. | | 392/395 |
| 5,263,274 A * | 11/1993 | Speed | | 43/1 |
| 5,299,376 A * | 4/1994 | Roberts | | 43/2 |
| 5,307,584 A * | 5/1994 | Jarvis | | 43/1 |
| 5,501,033 A * | 3/1996 | Wefler | | 43/131 |
| 5,555,663 A * | 9/1996 | Burgeson | | 43/1 |
| 5,744,106 A * | 4/1998 | Eagle | | 422/306 |
| 5,776,561 A * | 7/1998 | Lindauer | | 428/24 |
| 5,857,281 A * | 1/1999 | Bergquist et al. | | 43/1 |
| 6,102,301 A * | 8/2000 | Tiedemann | | 239/55 |
| 6,158,668 A * | 12/2000 | Burgeson | | 239/47 |
| 6,241,161 B1 * | 6/2001 | Corbett | | 239/58 |
| 6,340,120 B1 * | 1/2002 | Seymour | | 239/59 |
| 6,648,239 B1 * | 11/2003 | Myny et al. | | 239/44 |
| 7,188,786 B2 * | 3/2007 | Dodd | | 239/310 |
| 7,377,493 B2 * | 5/2008 | Thomas | | 261/30 |
| 7,419,102 B2 * | 9/2008 | Harris, Jr. | | 239/48 |
| 7,854,393 B2 * | 12/2010 | DiBello et al. | | 239/34 |
| 8,181,826 B2 * | 5/2012 | Wainwright | | 222/181.2 |
| 2003/0098362 A1 * | 5/2003 | Chuang | | 239/44 |
| 2007/0140923 A1 * | 6/2007 | Wiegand | | 422/124 |
| 2009/0307957 A1 * | 12/2009 | Gass et al. | | 43/1 |
| 2010/0187324 A1 * | 7/2010 | Feygin et al. | | 239/6 |

* cited by examiner

*Primary Examiner* — Len Tran
*Assistant Examiner* — Alexander M Valvis

(57) ABSTRACT

A scent dispenser is provided to dispense liquid scent during a hunt for wild game. The inventive scent dispenser uses age old scientific and natural phenomena to enhance the speed of the wind. The provided dispenser uses a venturi wind channel to accomplish a wind speed increase. Supported at its center of gravity from above or below, allowing rotation, the funnel shaped wind channel is continuously aligned with the wind direction by a wind vane. Liquid scent is introduced in the constricted section of the venturi wind channel where the wind velocity is increased. This increased wind speed, and continuous alignment to wind direction, enhances the vaporization of liquid scents that attract wild game, and that mask the scent of a hunter from the wild game's keen sense of smell.

10 Claims, 7 Drawing Sheets

WIND DIRECTED SCENT DISPENSER

This application is a continuation of Provisional Application No. 61/395,750 filed May 17, 2010 entitled "WIND DIRECTED SCENT DISPENSER". This invention relates to dispensing liquid scent during a hunt for wild game.

RELATED U.S. APPLICATION DATA

Continuation of Provisional Application No. 61/395,750 filed on May 17, 2010.

TECHNICAL FIELD

The present invention is used to dispense liquid scent during a hunt for wild game. Use of scents while hunting is an effective way to make a hunter more successful. Scents are available commercially that attract wild game, and that mask a hunter's scent from wild game's keen sense of smell.

BACKGROUND OF THE INVENTION

Scents used for hunting come in many forms. Burnable incense type, solid waxy sticks applied by rubbing, dryer sheets used in a clothes dryer to scent clothing, powders sprayed into the air, and small solid wafers are some of the more recent developments. Probably the oldest and most widely used form of hunting scent is liquid. These liquid scents are derived both naturally and synthetically. Some come in highly concentrated forms. Attracting scents that smell like the animal's preferred foods are readily available, with acorn and apple scents being popular for deer hunting. Sexual attractants are used to lure males during the breeding season. These sexual attractant scents are formulated from fluids such as the urine of a female in its estrus cycle. Deer, moose and elk all respond to these scents during breeding season. Masking scents are often used along with attractants to mask a hunter's scent from the quarry's keen sense of smell. These can be applied directly to the hunter or distributed around the hunting site. There are scents available to make a hunter smell like everything from dirt to a skunk, with the effectiveness of a specific smell being a matter of opinion.

The concept of a venturi is that a gradual reduction or constriction in the cross section of a fluid flow channel causes a proportional increase in the velocity and kinetic energy of the flowing fluid, and a decrease in pressure in the constricted section of the channel. This phenomenon, described by Bernoulli's Principle, was first discovered by mathematician, physicist and physician Daniel Bernoulli of Switzerland, who died in 1782. An Italian physicist named G. B. Venturi, who died in 1822, also did research on this phenomenon. Venturi's invention of the Venturi-Tube is still used in various forms to measure the flow of fluids, and his name is most often attached to fluid flow channels of this shape or type. This age old science is still used today to adjust velocity and pressure in fluid flow channels.

A fluid can be defined as any substance, liquid or gas, that is capable of flowing and which changes its shape at a steady rate when acted on by a force. Air is a mixture of nitrogen, oxygen and other fluid gases that surround the earth to form its atmosphere. Air is a fluid that responds to the effects of the phenomenon described by Bernoulli's Principle.

A wind vane is defined as a device rotating freely in a horizontal plane and so mounted and formed as to point into the wind. Also referred to as weather vanes, these devices have been used for centuries to monitor wind direction and as alignment devices for windmills, turbines and pumps. Anywhere alignment used to a flowing fluid is needed, a form of this device might be used.

DESCRIPTION OF PRIOR ART

Other inventive scent dispensers make use of fans and heating elements to increase volatization of liquid hunting scent. U.S. Pat. No. 5,161,646 uses a heated wick that is submerged in the liquid scent. It requires a power source to heat the wick. U.S. Pat. No. 5,744,106 heats the liquid scent by means of an ignitable fuel such as paraffin. U.S. Pat. No. 6,038,805 vaporizes the scent by heating it with a candle. U.S. Pat. No. 5,970,643 makes use of an electric fan to vaporize the liquid scent. It would require a power source and definitely wouldn't fit in the hunter's pocket. U.S. Pat. No. 6,443,434 B1 makes use of a heating element and a fan to enhance vaporization of the liquid scent. A solar panel and battery are used for a power source. U.S. Pat. No. 5,305,541 uses an electric fan to promote vaporization of the liquid scent by routing the vapor through a box with a heater and series of conduits and valves. U.S. Pat. No. 6,050,016 is another inventive dispenser that uses an electric fan to increase volatization. It is simpler than most of the others but still requires a power source and would also lack desired compactness. U.S. Pat. No. 5,359,801 utilizes a heat source to increase volatization of the liquid scent. It is unique in that it uses a combustible fuel as a heat source, with propane being preferred.

No matter how well these innovative scent dispensers accomplish the task of volatization, wind is still needed to carry the scent to the wild game. A dispenser that operates by quietly using the wind, and only the wind, for enhanced volatization, and continuously automatically sends all scent emission directly downwind can be appreciated by those skilled in the art and by any hunters that might use such a device. As will be described in this disclosure, the present invention has attributes the fore-mentioned hunting liquid scent dispensers either partially or completely lack.

SUMMARY OF THE INVENTION

The present invention uses a gradual reduction in the size of an air flow channel to increase the velocity of the wind. A liquid scent used for hunting is introduced in the reduced portion of the wind channel to increase volatization of the liquid. The air channel is aligned to the wind direction by a wind vane that continuously maintains alignment with the wind for optimum air flow through the channel. This enhanced air flow thereby produces more vaporization of the liquid scent, sending more scent directly downwind of a hunter for luring wild game, or for masking the hunter's scent from the wild game.

DESCRIPTION OF THE INVENTION

Figure 1:
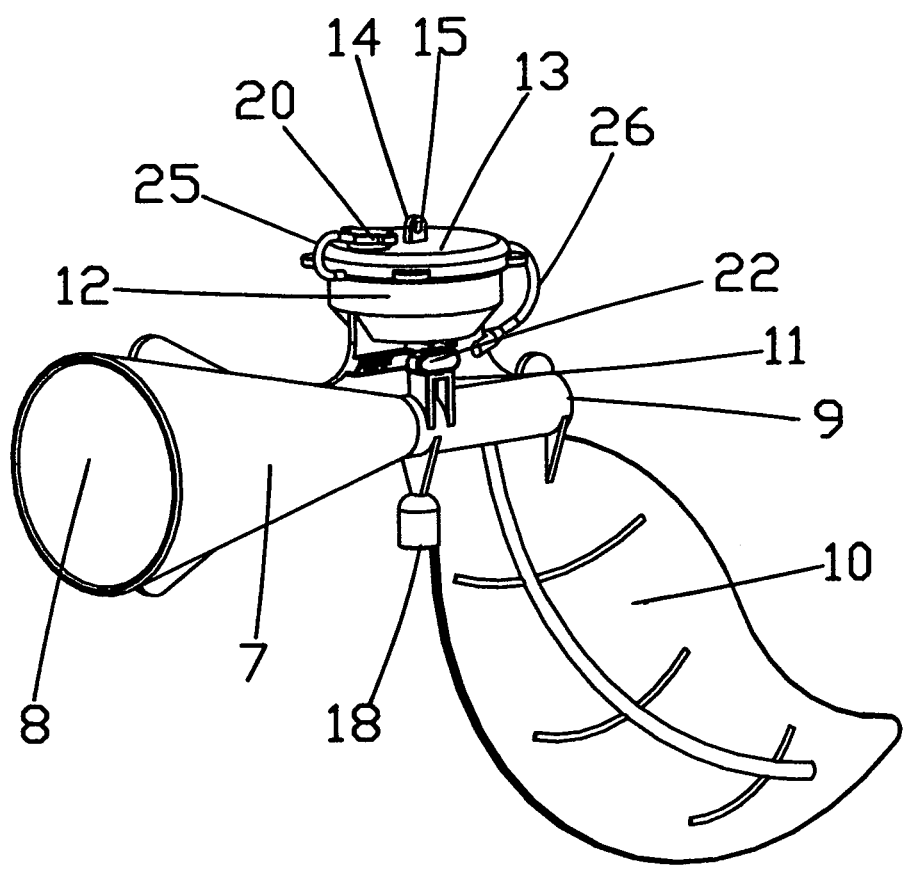
FIG. 1 is a perspective view of the scent dispenser.

The preferred embodiment of the present invention is based on a venturi or funnel shaped wind flow channel. The scent dispenser body is comprised of five main components of function, injection molded of resilient polymeric material as one piece. The five functional components are the funnel shaped wind channel 7, the wind alignment vane 10, the liquid flow passage 21, the flow control valve 11 and the scent reservoir 12. See FIG. 1. The liquid scent is contained in the reservoir 12 by a removeable reservoir cap 13, also injection molded of a resilient polymeric material. The cap having a small central projection 14 from the top, with a lateral aperture 15 through this projection at the dispenser assembly's center of gravity. The preferred embodiment is supported at its center of gravity. It is suspended from a structure such as a tree limb 27 on a fine string or line 16 connected through the aperture 15. This fine string or line 16 is flexible enough to easily twist as the wind vane aligns the dispenser with the wind direction. See FIG. 2. A free turning member such as a fishing line swivel could also be part of this link with the supporting structure. Since an above supporting structure such as a tree limb 27 is not always available at a desired hunting location, the dispenser can also be supported at its center of gravity by a small diameter rod 17 inserted into the aperture 18 below the wind channel 7. The opposite end of this rod 17 is then vertically pushed into the ground 28 wherever the hunter wants it. See FIG. 3. By supporting the dispenser at its center of gravity it is allowed to freely turn to align with wind direction when the wind vane 10 is acted on by the wind. This support of the liquid scent dispenser at the center of gravity, provides a level wind channel 7 under most wind conditions. Also positioned on the top of the cap is a small venting aperture 19 passing through the reservoir cap 13 into the reservoir for venting to induce flow of the liquid scent. This venting aperture 19 is covered with a removeable vent cap 20 when the dispenser is not in use. The vent cap 20 is linked to the reservoir cap 13 by an integrally molded connector 25 to prevent loss when the vent cap 20 is off during use. A similar link 26, also integrally molded to the canister cap 13, attaches the reservoir cap 13 to the scent dispenser body.

Figure 7:
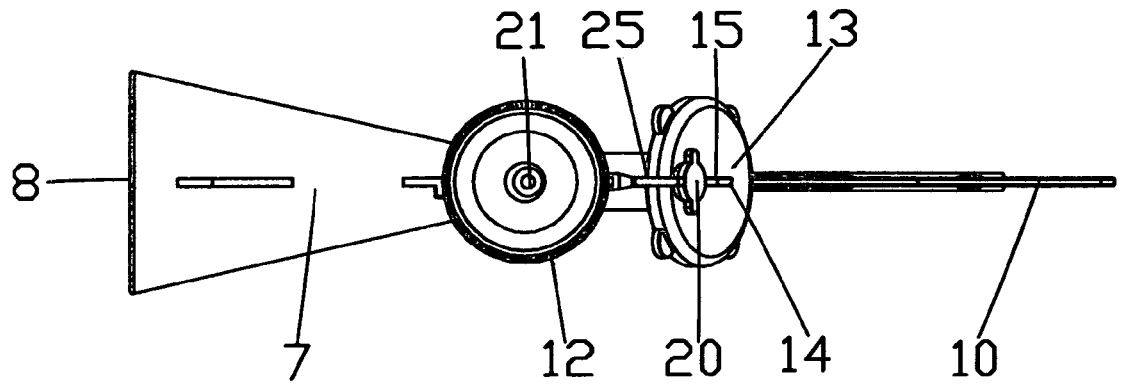
FIG. 7 is a top view of the scent dispenser with the liquid scent reservoir cap off.
Figure 8:
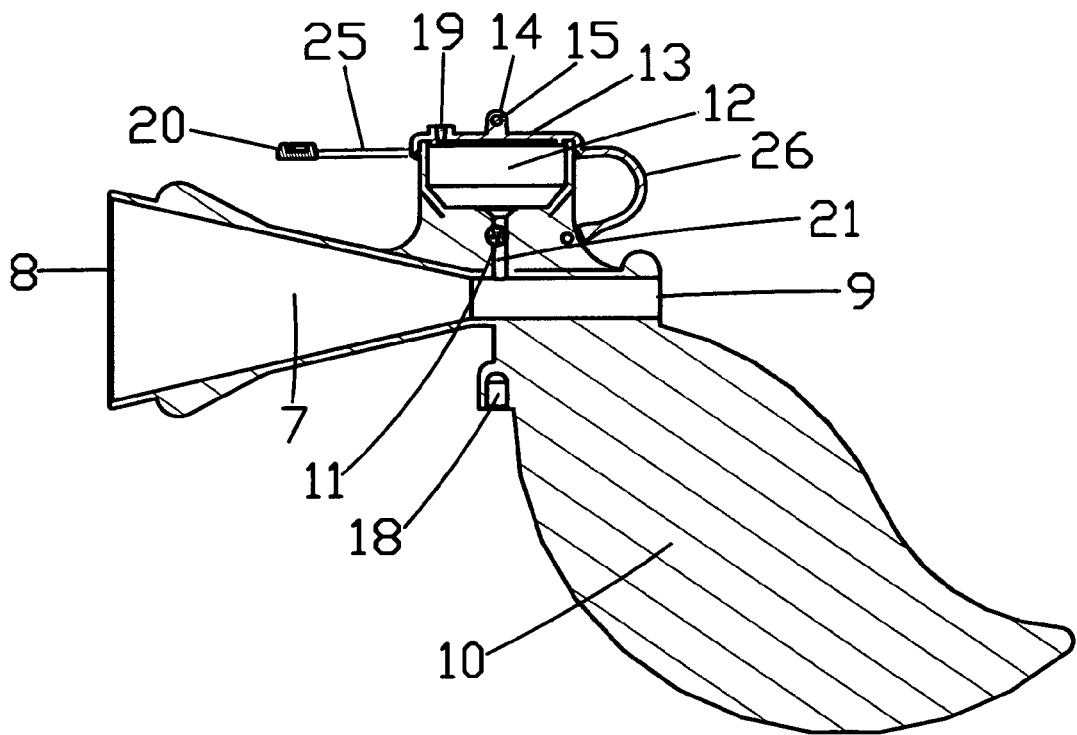
FIG. 8 is a side view of the scent dispenser, sectioned at the center line.

The function of the present invention is accomplished by the flow of the liquid scent from the reservoir 12 to the reduced area of the wind channel 7 through a liquid scent passage 21. FIG. 7 is a top view of the scent dispenser with the reservoir cap 13 off, showing the liquid scent passage 21. FIG. 8 is a sectioned view of the dispenser split at the center line of the wind channel 7, the liquid scent reservoir 12, the liquid scent passage 21 and the wind vane 10.

The venturi or funnel wind channel 7 is continuously aligned with the wind by the wind vane 10, with the wind entering the larger end 8 and exiting the smaller end 9 of the funnel wind channel 7. The liquid flow is gravity induced by the location of the liquid scent reservoir 12 above the wind channel 7. Flow will also be enhanced by the vacuum effect of the lowered pressure in the constricted section of the wind channel 7, where the liquid scent enters it. Between the liquid reservoir and the wind channel 7, the flow of the liquid scent through this liquid flow passage 21 is interrupted by a flow control valve 11. This flow control valve 11 allows a variable flow rate to adjust for the wind speed and the hunter's flow rate preference, or to stop liquid scent flow completely for transport.

The inventive scent dispenser can vaporize more liquid the higher the wind speed. The adjustment of flow rate is accomplished by a valve stem 22 that passes through a hole in the dispenser body perpendicular to the liquid scent passage 21 to form the valve. The valve stem 22 rotates one hundred eighty degrees on its diametral axis to provide variability from full on to off. FIG. 1 shows the dispenser in its transport configuration with the valve stem 22 in its off position at nine o'clock, and the vent hole covered by its vent cap 20.

Figure 2:
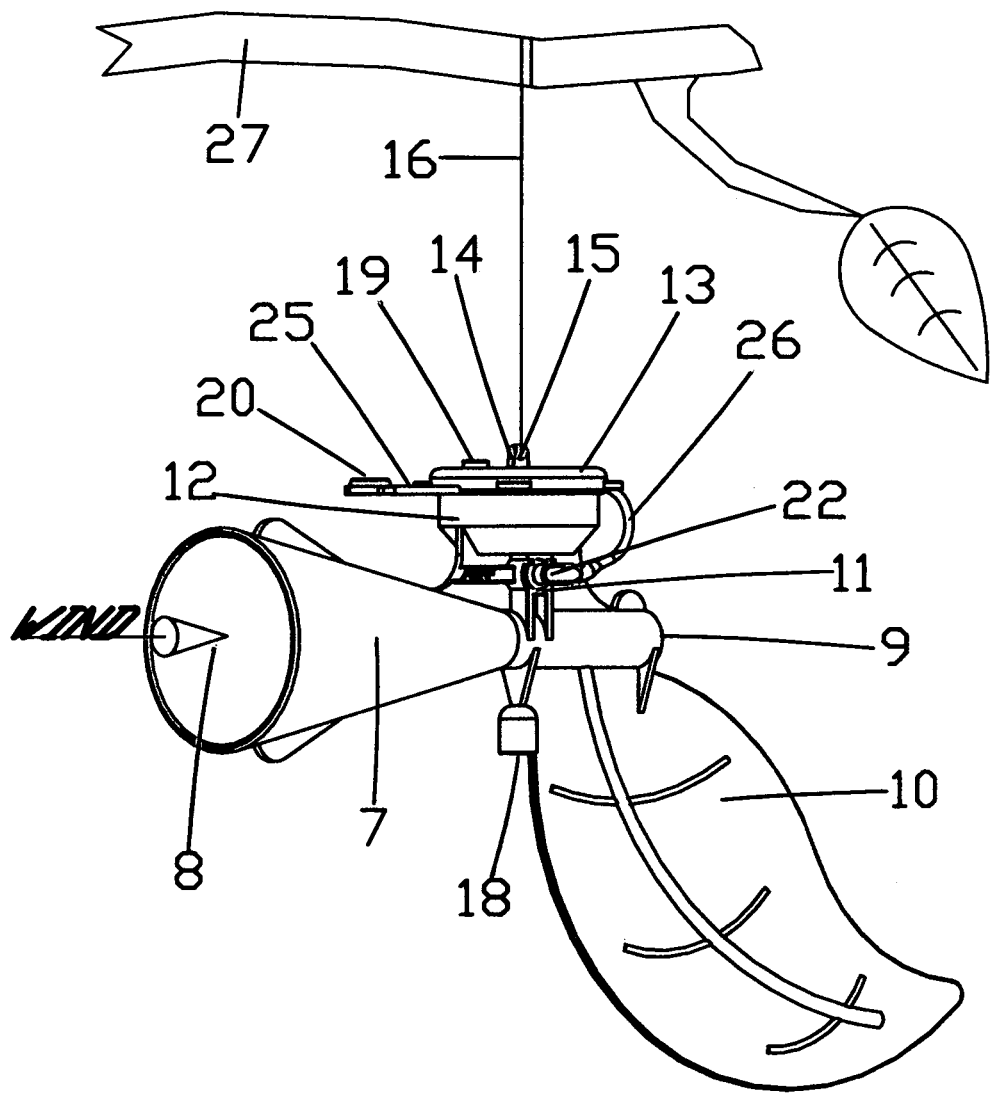
FIG. 2 is a perspective view of the scent dispenser as in use, suspended from above.
Figure 3:
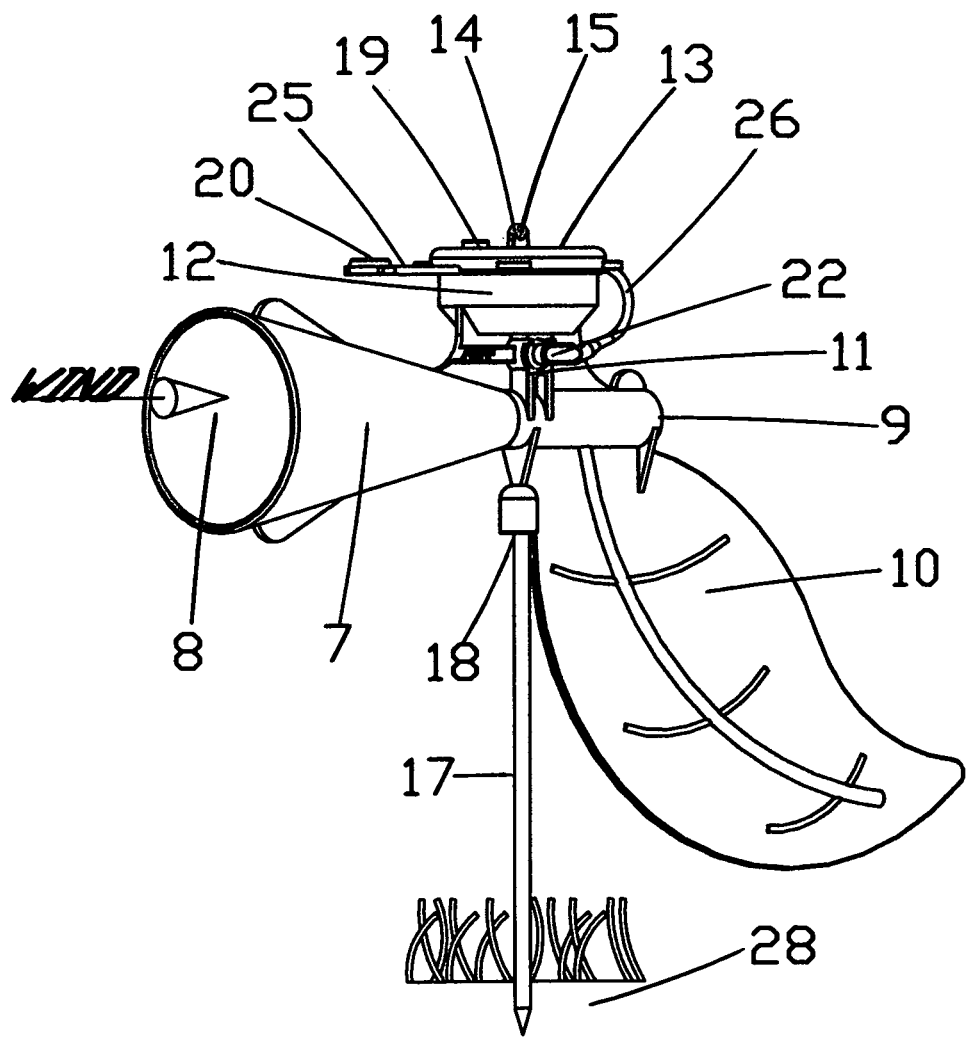
FIG. 3 is a perspective view of the scent dispenser as in use, supported from below.
Figure 4:
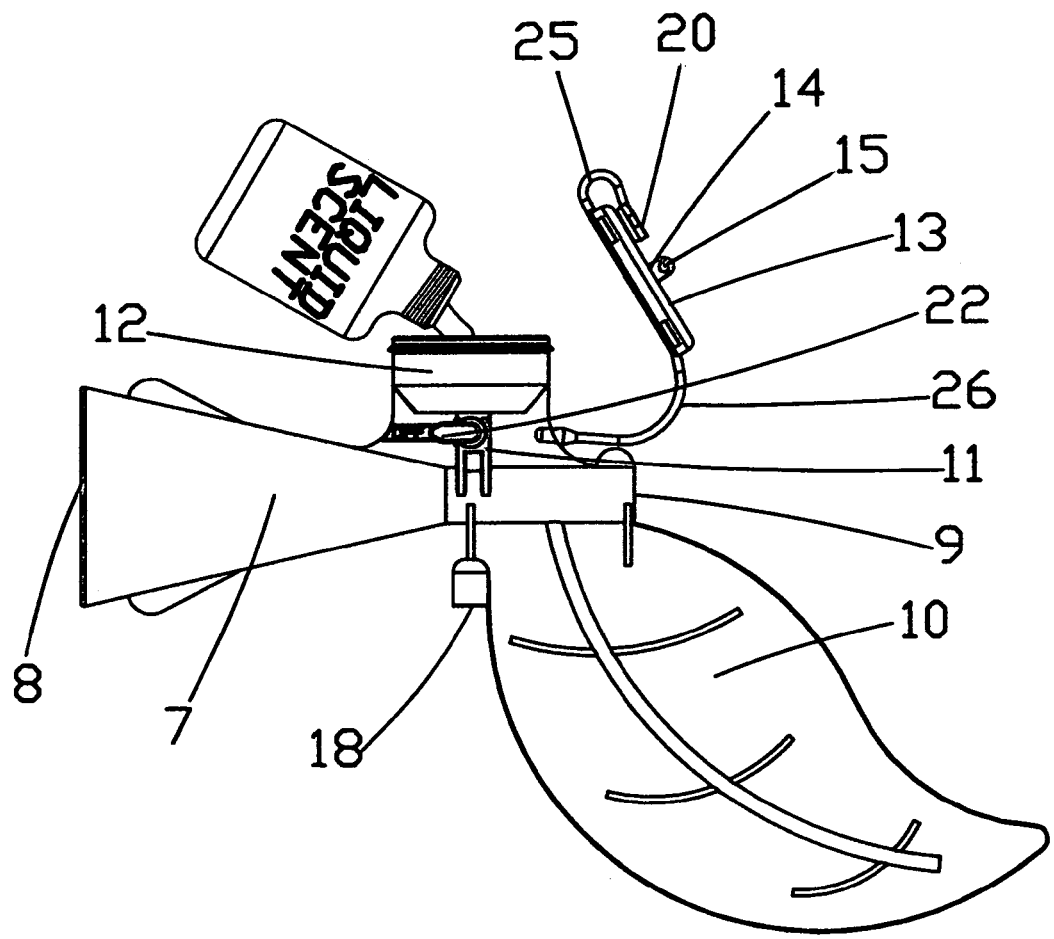
FIG. 4 is a side view of the scent dispenser with reservoir cap off, being filled.
Figure 5:
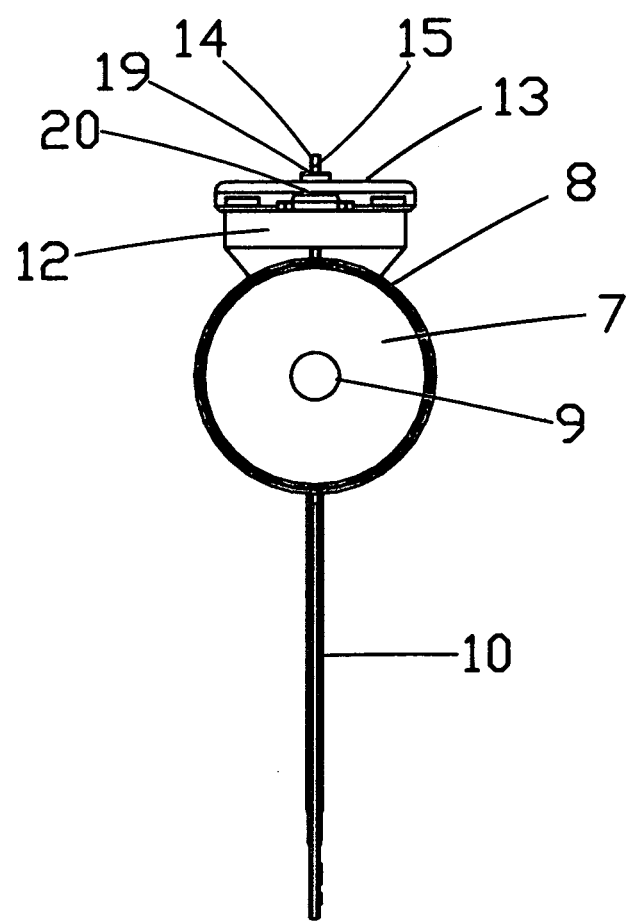
FIG. 5 is a view of the scent dispenser from the larger wind inlet end of the air flow channel.
Figure 6:
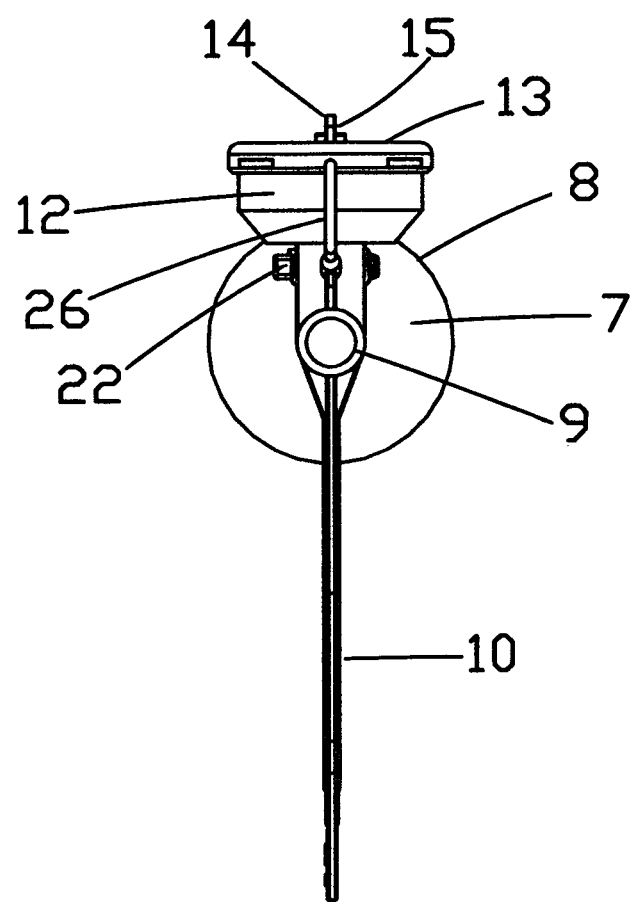
FIG. 6 is a view of the scent dispenser from the smaller wind outlet end of the air flow channel.

FIGS. 2 and 3 show the dispenser with in-use configurations, with the valve stem 22 in the full on position, at three o'clock, pointing downwind, and the vent cap 20 off. Between these two positions, three o'clock and nine o'clock, the flow control valve provides a user selected variable flow rate, with a six o'clock position being half way on.

Vaporization of the liquid scent could be further enhanced with the addition of a heat source. A battery powered heat coil or a chemical heat pad might be used as the heat source. This could be located inside or outside of either the scent reservoir, the venturi, or both, as long as the necessary balance for the function of the wind vane is maintained. Heating the liquid scent dispenser would allow the present invention to be used in freezing temperatures.

Those skilled in the art will recognize the possibility for other structural forms and configurations of the present invention. For instance, the alignment wind vane 10 need not be in the shape of a leaf and could be located above the venturi wind channel 7 as long as the necessary balance, position and functional thickness of the wind vane 10 is maintained. Many will realize that the aligning wind vane 10 is also useful to hunters as an accurate wind direction indicator.

The general size of the scent dispenser or any of its components could vary. Air flow channel size, cross-sectional shape and angular configuration of the constriction could vary, with, non-funnel, non-venturi air flow channels being functional options. The liquid scent could be introduced anywhere in the venturi wind channel 7 and not just in the reduced section. The liquid scent reservoir 12 could also be located below the wind channel 7 with the scent being introduced into the wind channel 7 by evaporation. The present invention could also be made of other materials or combinations of materials. It would be feasible to construct all or part of the scent dispenser from wood, paper, metal, cardboard or other practical materials. Any of the physical attributes could vary or be changed completely without departing from the spirit and scope of the present invention. The present invention being a liquid scent dispenser that makes use of a venturi or funnel shaped wind channel 7 to enhance volatization of liquid scent used in hunting. The present invention using a planar wind vane 10 to align the wind channel 7 with the wind direction.

The present invention having liquid scent introduced at the constricted section of the funnel shaped wind flow channel 7 where the wind velocity is increased. The scent being introduced from above the wind channel 7 by gravity and by the reduced pressure in the constricted section of the funnel wind channel 7. The present invention being supported at its center of gravity or balance point, either from above or below the dispenser, allowing free rotation about the vertical axis at its center of gravity or balance point. The alignment wind vane 10 could be omitted from the preferred structure without departing from the spirit and scope of the present invention. This would require a support of the inventive scent dispenser that could be manually aligned with the wind direction. This could be done on the ground or moveably attached to a structure.

The present invention has attributes a hunter needs in such a device. The present invention is entirely injection molded polymer, making it relatively inexpensive and durable. It is compact enough to fit a plurality in the pocket of a hunter. Being compact also makes the present invention less conspicuous to the keen eye of wild game. Its on or off function allows it to be filled with scent prior to the hunt and be conveniently carried in a pocket or pack to the hunting site, full of liquid scent. Enhanced vaporization of the liquid scent is accomplished with a venturi wind channel 7, without requiring electrical power or a heat source. The wind channel and its emitted scent stream are continuously aligned to the wind direction by the wind vane 10. It can be supported by a line 16 from above or on a stake 17 from below, allowing use in any hunting situation. Its simplicity and its on or off function allow it to be quickly and easily put in use at the hunting site, and turned off and stowed for transport at the end of the hunt. Since many liquid scents for hunting are based on biological fluids, spoilage or degradation of the scent retained on a wick or pad could occur, possibly making other scent dispensers ineffective. The present invention's flow control valve 11 can be turned off, leaving any remaining liquid scent in the sealed reservoir 12 for future use. The present invention's wind channel 7 can then be flushed of scent residue with water to avoid possible spoilage or degradation.

Please note that various changes, alternatives or modifications will become apparent following a reading of the foregoing description. It is intended that any such changes, alternatives or modifications that fall within the scope of the appended claims be considered part of the present invention.

What is claimed is:

1. A liquid scent dispenser used during a hunt for wild game comprising:
   A funnel wind channel with an inlet and an outlet, said inlet being larger than the outlet as to constrict the flow of air;
   A liquid scent reservoir, which contains a liquid scent positioned functionally above the funnel wind channel;
   A liquid scent flow passage connecting the liquid scent reservoir and the wind channel;
   Said liquid scent reservoir has a removable cap for refilling said liquid scent, said cap providing a support means at a center of gravity or balance point from above the liquid scent reservoir;
   A flow control valve is disposed within the liquid scent flow passage which allows a flow rate to be adjustable, said valve can be turned off leaving any remaining liquid scent in the sealed liquid scent reservoir;
   One or more planar wind vanes positioned at the outlet end of said funnel wind channel for the purpose of directing the liquid scent dispenser outlet in the direction of the wind.

2. A liquid scent dispenser used during a hunt for wild game, according to claim 1, wherein said liquid scent reservoir is cylindrical, axially perpendicular and central to said wind channel.

3. A liquid scent dispenser used during a hunt for wild game, according to claim 1, rotatably supported at center of gravity or balance point, from above by a suspension line, allowing free complete rotation on a horizontal plane about the vertical axis at the center of gravity or balance point.

4. A liquid scent dispenser used during a hunt for wild game, according to claim 1, wherein said removable cap has a functionally vertical projection from the top center of said cap, a lateral aperture through said projection central to said cap, thereto accepting a suspension line as said support at a center of gravity or balance point from above.

5. A liquid scent dispenser used during a hunt for wild game according to claim 1, wherein said one or more planar wind vanes are parallel or central to the axial center of said liquid scent reservoir and the axial center of said funnel wind channel.

6. A liquid scent dispenser used during a hunt for wild game comprising:
   A funnel wind channel with an inlet and an outlet, said inlet being larger than the outlet as to constrict the flow of air;
   A liquid scent reservoir, which contains a liquid scent positioned functionally above the funnel wind channel;
   A liquid scent flow passage connecting the liquid scent reservoir and the wind channel
   Said liquid scent dispenser having a support from below;
   Said liquid scent reservoir has a removable cap for refilling said liquid scent
   A flow control valve is disposed within the liquid scent flow passage which allows a flow rate to be adjustable, said valve can be turned off leaving any remaining liquid scent in the sealed liquid scent reservoir;
   One or more planar wind vanes positioned at the outlet end of said funnel wind channel for the purpose of directing the liquid scent dispenser outlet in the direction of the wind.

7. A liquid scent dispenser used during a hunt for wild game, according to claim 6, wherein said one or more planar wind vanes are parallel or central to the axial center of said liquid scent reservoir and the axial center of said funnel wind channel.

8. A liquid scent dispenser used during a hunt for wild game, according to claim 6, wherein said one or more planar wind vanes are parallel or central to the axial center of said funnel wind channel, shaped and positioned along the axial center at the constricted outlet end of the funnel wind channel, that when acted on by the wind, the wind directly enters the larger end of said funnel wind channel and exits the constricted, smaller outlet end of said funnel wind channel.

9. A liquid scent dispenser used during a hunt for wild game, according to claim 6, rotatably supported at the support of the center of gravity or balance point from below by a vertical support rod, allowing rotation on a horizontal plane about the vertical axis at the center of gravity or balance point.

10. A liquid scent dispenser used during a hunt for wild game according to claim 6, where said liquid scent dispenser has a diametrical cavity that is capable of accepting the support rod at the center of gravity or balance point.

* * * * *